US005447686A

United States Patent [19]

Seidner

[11] Patent Number: 5,447,686

[45] Date of Patent: Sep. 5, 1995

[54] METHOD FOR HEAT-TREATING WOOD AND WOOD PRODUCTS

[76] Inventor: Marc A. Seidner, 234 Conway Ave., Los Angeles, Calif. 90024

[21] Appl. No.: 261,715

[22] Filed: Jun. 17, 1994

[51] Int. Cl.[6] .................. A61L 2/06

[52] U.S. Cl. .................. 422/26; 422/1; 34/389

[58] Field of Search .................. 422/1, 26, 27, 38, 40; 43/124, 130; 34/380, 389, 396, 218, 219; 144/271, 364, 380

[56] References Cited

U.S. PATENT DOCUMENTS

| | | | |
|---|---|---|---|
| 84,733 | 12/1868 | Cowling | 422/39 |
| 102,665 | 5/1870 | Douglas | 422/1 |
| 148,752 | 3/1874 | Pine | 144/271 |
| 3,070,896 | 1/1963 | Knudson et al. | 34/219 |
| 3,422,545 | 1/1969 | Wilson | 34/403 |
| 3,867,765 | 2/1975 | Foster | 34/380 |
| 3,939,573 | 2/1976 | Berti | 34/471 |
| 4,017,980 | 4/1977 | Kleinguenther | 34/396 |
| 4,027,401 | 6/1977 | Fairbanks, Jr. | 34/410 |
| 4,620,373 | 11/1986 | Laskowski et al. | 34/406 |
| 4,698,305 | 10/1987 | Hansson | 435/171 |
| 4,853,241 | 8/1989 | Dörnemann | 422/28 |

OTHER PUBLICATIONS

Steinhagen, et al., "Heating Time Charts for Frozen and Nonfrozen Vener Logs", *For. Prod. J.* 30(4) pp. 27–29, Apr. 1980.

Proposed Rules, *Federal Register*, vol. 59, No. 13, Jan. 20, 1994, "Importation of Logs, Lumber, and Other Unmanufactured Wood Articles".

Steinhagen, H. Peter, "Heating Time Simulation for Frozen and Unfrozen Wood," pp. 33–37, 1986.

*Primary Examiner*—Robert J. Warden

*Assistant Examiner*—Theresa T. Snider

*Attorney, Agent, or Firm*—Pretty, Schroeder, Brueggemann & Clark

[57] ABSTRACT

The present invention is embodied in a method for heat-treating pieces of wood or wood products, such as logs, lumber or wood chips with steam or hot water to kill any plant pests present in the wood or wood products. The pieces are loaded into a hold of a ship equipped to introduce steam or hot water into the hold. In some embodiments, the ship is also equipped to recycle the spent steam or water. The pieces are then contacted with steam or hot water to raise the temperature of the pieces to a sufficient level for a sufficient period of time to kill any plant pests that might be present.

36 Claims, 2 Drawing Sheets

METHOD FOR HEAT-TREATING WOOD AND WOOD PRODUCTS

BACKGROUND OF THE INVENTION

1. Field of the Invention

This invention relates to the treatment of wood and wood products to kill plant pests and preserve the fresh-cut characteristics of green wood. In particular, it relates to subjecting raw or green wood and wood products to heat for a sufficient time to destroy any plant pests that may have infested the wood or wood products, while preventing cracking, checking or other deterioration of the wood or wood products.

2. Discussion of the Related Art

Already, the United States has become the world's leading importer of wood and wood products. In 1990, the United States imported the equivalent of 34.4 million cubic meters of logs, lumber and other wood products.

The United States' demand for imported wood and wood products can only be expected to increase. Domestic logging companies are facing increasing challenges from conservation groups. Conservationists oppose many tree harvesting practices, especially clear cutting. In addition, concern over habitats for wildlife and preservation of stream beds for fish has impacted the supply of trees for harvest. Unanswered questions about replacement of old growth/diversified forests and the costs of logs and logging have changed the industry's economics greatly. Accordingly, domestic commercial forest lands are projected to decrease by about 4 percent over the next 50 years. The resulting shortage will need to be met in part by importing wood and wood products.

Potential supplies for additional wood and wood products are located in such far away places as the former Soviet Union, New Zealand, Chile and Brazil. An obstacle to importing green wood and wood products from such distant locations is the danger that the foreign products could introduce and spread exotic plant pests throughout the United States.

At the same time, the United States has become the world's largest exporter of wood and wood products. However, there are also a number of plant pests native to the United States, such as nematodes occasionally found in southern pines, that are not found in overseas forests. These pests create an obstacle to exporting still more timber grown in the United States to overseas markets.

A number of methods are known for destroying plant pests. Unfortunately, they all suffer from drawbacks, especially when considered in the context of treating wood and wood products to be transported overseas. For example, it is known that heat-treating wood and wood products, typically in a kiln with an attendant reduction in the moisture content of the material, is an effective method for killing plant pests. Such heat-treatment processes require bringing the center of the material to a certain minimum temperature for a certain minimum period of time so as to dry the material without causing any cellular or structural degradation.

Therefore, kiln-drying processes have been employed that are best suited to carefully and precisely treat relatively small amounts of material. They are typically used for treating wood lots of up to about 350 cubic meters or equivalent volumes of wood products having a relatively thin cross-section such as sawn lumber having a cross-sectional dimension of about 2"×10". Rarely is lumber having a cross-sectional dimension in excess of 6"×10" kiln dried.

Furthermore, the capital cost of a suitable kiln is great, running from at least many hundreds of thousands of dollars up to millions of dollars. And it is often the case, that far away countries, rich in raw materials such as timber, do not have the facilities to saw mill logs into lumber, let alone kilns or other costly treatment facilities. It is a further drawback of kilns and other treatment facilities, that once constructed they are fixed in location and point of service. Consequently, a large number of such facilities would be required to treat all the lumber found in disparate locations spread across the globe.

Even when wood and wood products are treated overseas, there remains a risk of reinfestation by plant pests. Unless the wood and wood products' environment is carefully monitored and controlled, reinfestation can occur before the materials are loaded aboard the ship, or even after they are loaded, if the ship contains infested cargo that has not been treated.

One approach to the problem is fumigating wood and wood products once a ship carrying a load of wood or wood products has completed its journey. This is a customary practice of eliminating pests in the both the United States and other countries, such as Japan. Fumigation effectively controls plant pests that may be associated with the surface and subsurface of debarked logs and other wood products. Fumigation may not be effective in killing other plant pests that bore deep into the wood or in killing microscopic pests that live in the wood's cells. Another significant drawback of fumigation is that it has been known to pose a health risk to people and the environment.

Additional disadvantages of fumigation include the expense of the fumigant. And, because of the potential health hazard of the fumigant, most often methyl bromide, fumigation can only be carried out under carefully controlled circumstances, usually, once the ship has entered port and the crew has been safely removed. This further adds to the environmental risk, time and expense involved in importing wood and wood products which are treated in this manner.

It is also known that boiling or steam-treating logs, so they may be softened and readily peeled in the initial steps of making veneer or plywood, can produce a side benefit of pest treatment. This land-based process, however, is not used for treating large quantities of logs or logs typically longer than about 10 feet. Nor is such boiling or steam-treating used for wood or wood products that are made into lumber or not immediately thereafter turned into veneer or plywood. Furthermore, this process takes place only after importation of the logs and usually at a location in or near domestic forests, where plant pest risks pose the greatest threat to domestic trees.

Another obstacle to importing green wood and wood products, especially logs, lumber, wood chips or wood strands from across the seas is the condition of the wood or wood product when it arrives at its destination. A freshly cut log has a moisture content of about 50%. As a general rule, because of the evaporation of surface and internal moisture, the longer the period of time since the tree has been cut, the drier the wood becomes. The increasing dryness of a log is a drawback in such subsequent manufacturing processes as the manufacture of lumber or veneer. If care is not taken during the period after felling the tree and continuing up through its shipping, moisture variations cause degrees of wood degradation such as cracks and checks. Moreover, incipient rot can form. These phenomena all make portions of the wood unusable in or less valuable for subsequent fabrication, such as fabrication into lumber or veneer or oriented strand board. Similarly, if care is not taken with wood chips or wood strands, there can be a significant loss of fiber, which can destroy or greatly reduce the value of the wood.

Accordingly, there has existed a definite need for a safe, effective and inexpensive method for eliminating significant plant pest risks from green wood and wood products, including large volumes of green logs, sawn lumber, wood chips and wood strands transported overseas. There has also existed a need for a method which minimizes the risk of reinfestation of plant pests after the initial treatment. There has existed a still further need for a method for maintaining the fresh-cut characteristics of wood and wood products delivered from overseas by reducing the incidence of cracks, checks and incipient rot or, in the case of wood chips or wood strands, by minimizing fiber loss. The present invention satisfies these and other needs and provides further related advantages.

SUMMARY OF THE INVENTION

The present invention is embodied in a method for heat-treating pieces of wood or wood products, such as whole green logs, sawn lumber, or wood chips or wood strands with steam or hot water to kill any plant pests present in the material, while preserving the fresh-cut characteristics of the pieces. The pieces are loaded into at least one hold of a ship equipped with means for producing steam or hot water and means for introducing the steam or hot water into the hold in a measured or controlled manner. In some embodiments, the ship is also equipped with means for recycling the spent steam or water back to the means for producing the steam or hot water for subsequent reintroduction to the cargo after reheating.

The pieces are then contacted with steam or hot water in the hold to raise the temperature of the pieces to a sufficient level for a sufficient period of time to kill any plant pests that might be present. For example, it has been found that raising the temperature of the center of the pieces of wood to at least 56° C. and maintaining that temperature for at least 30 minutes is effective. In some embodiments the steam or hot water additionally contains a chemical wood-treating ingredient, such as a wood preservative, a fire retardant, a fumigant, a nematocide, a fungicide or an insecticide.

DESCRIPTION OF THE PREFERRED EMBODIMENTS

Figure 1:
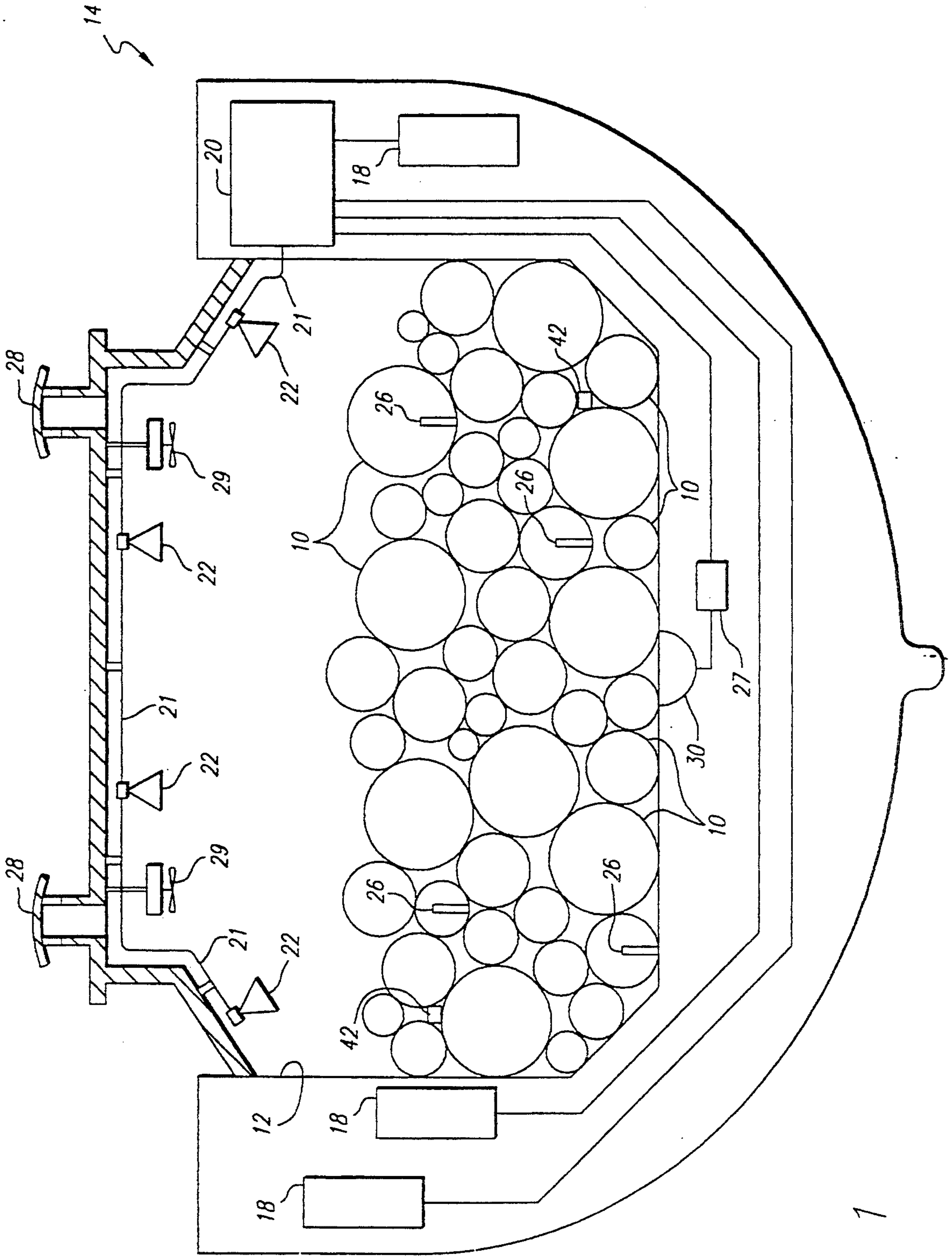
FIG. 1 is a cross sectional view of the hull of a ship loaded with logs and outfitted to treat the logs in accordance with the invention.

With reference now to the drawings, and in particular to FIG. 1, there is illustrated a shipment of logs 10 located in a hold 12 of a ship 14. While logs are illustrated in FIG. 1, the method in accordance with the invention is useful with a wide variety of wood and wood products. As used hereinafter and as used in the claims, the term wood should be construed broadly to include both wood and wood products. Accordingly, examples of wood that can be treated in accordance with the invention include whole trees, cut trees, or any portion of a tree, including logs, other than its leaves, flowers, fruits, buds or seeds. Also treatable are lumber (logs that have been sawn into boards, planks, or structural members, such as beams and timbers), cants, flitches, wood chips, wood strands and the like. The only limitation on the wood to be treated is that, as will be discussed in greater detail, it must be capable of being loaded aboard the ship so that steam or a hot water shower can be caused to permeate the wood and raise its temperature throughout.

The method in accordance with the invention is particularly useful with wood that is raw or green, i.e., that is substantially unprocessed or unmanufactured. The wood can, however, advantageously undergo some primary processing before being loaded aboard the ship. For example the wood can be cleaned (soil, limbs, and foliage removed), debarked, rough sawn (bucked or squared), rough shaped, chipped (pulp or strands), sprayed with a fungicide or an insecticide or fumigated. And, if desired, the method can be employed with wood that has been sawn into lumber or otherwise further processed or manufactured. In a preferred embodiment, the wood is debarked, since removal of bark facilitates the heat-treatment process.

Given the absence of facilities for heat-treatment, with or without moisture reduction, in many originating countries, it is an important advantage of the method in accordance with the invention that it enables treatment of wood, before it reaches the United States or other importing country. This is an important feature, because wood is more vulnerable to plant pest attacks the longer it remains untreated. Moreover, early treatment reduces the opportunity for plant pests that may be associated with an individual piece of wood to escape to surrounding areas or contaminate neighboring materials. Accordingly, the phytosanitary safety of wood is enhanced, because any plant pests initially present are treated before the wood enters the United States or other importing country.

It is also a distinct advantage of the method in accordance with the invention that it can be used to treat the large quantities of wood loaded into the holds of seagoing vessels. Typically, the combined storage capacity of the holds of seagoing vessels is from about 15,000 to about 20,000 cubic meters, even up to 35,000 cubic meters total of wood depending on the size of the vessel and number (usually three to five) and configuration of holds. Alternatively, a portion of the vessel's holds can be suitably partitioned and any lesser volume of wood can be effectively treated. It is a further advantage of the invention that the deck space of the ship can still be used for carrying other cargo and that this other cargo will not be effected by the heat-treatment process undertaken in the ship's hold.

As shown in FIG. 1, the logs are loaded in a customary manner for normal storage of such materials aboard seagoing vessels. Alternatively, the logs can be loaded using a plurality of spacers or, in the case of lumber, with breathing strips (not shown). The spacers or breathing strips are arranged to facilitate a flow of hot water through the material to be treated.

Water supplied from containment or storage tanks 18 is fed to a heating apparatus 20, such as a hot water heater, and heated to form hot water having a temperature from about 60° C. to about 90° C., preferably at least about 65° C. The hot water is directed from the hot water heater, through pipes 21, to a plurality of nozzles 22. The nozzles introduce a hot water shower into the hold 12. The extended and continuous application of the hot water shower envelops and penetrates logs 10 raising their temperature. Additionally, the natural movement of the sea-going vessel helps ensure good water coverage and heat dispersion throughout the logs.

The logs 10 are subjected to the hot water shower for a sufficient period of time to kill any plant pests that may be present. This can be accomplished by raising the temperature of the center or the logs to at least 56° C. and maintaining the logs at that center temperature for at least 30 minutes. It has been discovered that the combination of the gravitational flow of water and the natural heat transfer conductivity arising because of the water content of the green wood material provides an efficient and effective means for carrying out the heat-treatment. The heat-treatment is useful against essentially all plant pests in or on the wood, including insects in all stages, even deep wood borers not removed by surface treatments, fungi and nematatodes.

It is yet another advantage of the method in accordance with the invention that the pressure in the hold during treatment is generally, simply, ambient pressure. In some embodiments, however, higher pressures can be employed in order to facilitate the process.

Thermocouples 26 are placed variably throughout the hold into the centers of a representative sample of the logs to detect the temperature at their centers. The thermocouples are operatively connected to a control means (not shown) that monitors and enables the effective regulation of the flow of the hot water onto the hold 12 to achieve the appropriate treatment desired.

It is another distinct advantage of the method in accordance with the invention that the time it takes to treat the wood is of less practical importance, than in land-based treatments. Given the duration of overseas transit, even the largest volume of the largest logs can be brought to a sufficient temperature for a sufficient length of time to ensure that all plant pests are controlled.

Pump 27 and vents 28 allow the removal of the water that accumulates in the hold and the escape of the humid atmosphere. They enable the hold to be dehumidified, if desired, once the treatment is completed. In some embodiments, dehumidification is further aided by fans or blowers 29.

Located on the bottom of the hold 12 is at least one filtered collection well or trough 30. As the hot water falls, it enters the collection trough, is filtered and then is recycled back to the hot water heater 20, thus minimizing the amount of water required for the process.

Figure 2:
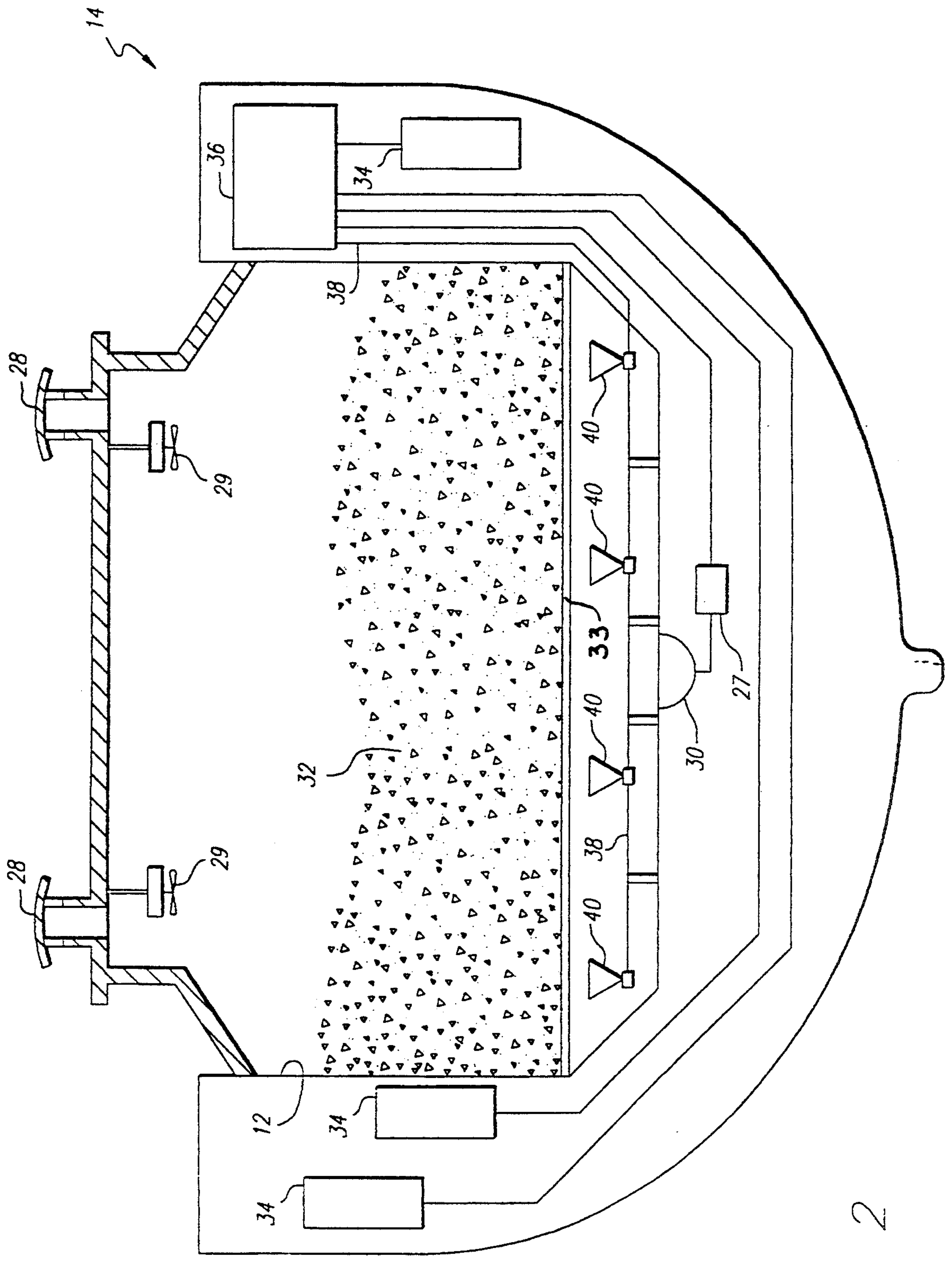
FIG. 2 is a cross sectional view of a portion of the hull of a ship loaded with wood chips or wood strands and outfitted to treat the material in accordance with the invention.

Turning now to FIG. 2, there is shown an embodiment for steam-treating wood chips or wood strands 32 loaded on top of grate 33 located in the bottom portion of hold 12. In this embodiment, water supplied from containment or storage tanks 34 is fed to a boiler 36 and heated to form steam. The steam is then directed from the boiler, through pipes 38, to a plurality of upwardly-directed nozzles 40 located beneath the grate. The nozzles inject the steam up into the portion of hold 12 loaded with the wood chips or wood strands. The steam then envelops and penetrates the wood chips or wood strands to raise the temperature of the woods chips or wood strands to a sufficient level for a sufficient period of time to kill any plant pests that may have been present.

A still further advantage of the process in accordance with the invention is that the risk of reinfestation after the initial heat-treatment is substantially eliminated. Since the entire load is heat-treated, within a singular containment vessel (the hold of the ship), at the same period of time, there is little risk of recontamination from sources within the ship. And since the ship is at sea, there is little risk of contamination from sources outside the ship.

In some embodiments, the steam or the hot water stream contains at least one chemical wood-treating ingredient which will penetrate the wood along with the steam or hot water. For example, the steam or hot water can include conventional fumigants, nematocides, fungicides, insecticides and the like. While these phytosanitary chemical additives are usually used in topical fashion in lieu of a heat treatment process, their inclusion during the process in accordance with the invention provides a greater measure of penetration into the wood which enhances or prolongs the chemical's effectiveness. Other chemical additives such as wood preservatives, fire retardants and the like can be added during the heat treatment process as an added benefit.

It is yet another benefit of the process in accordance with the invention that the moisture content of the logs 10 is controllable. By having a predetermined or maintained moisture content, the logs can be preserved or kept closer to their fresh-cut state for a longer period of time and under a greater variety of environmental conditions than has previously been possible.

As seen in FIG. 1, electrical conductivity or moisture meters 42 are attached onto the surface and into the interiors of a representative sample of logs 10. As is well known in the art, the electrical conductivity of wood is a measure of its moisture content. Accordingly, the electrical conductivity meters are operatively connected to the control means which enables an accurate measure of the effect of the hot water shower. This allows the moisture content of the logs to be maintained at a predetermined level or levels during long voyages or across latitudes of varying ambient temperatures and humidities.

By maintaining the logs' moisture content close to their original fresh-cut level of about 50% or by reducing their moisture content to a level of from about 30% to about 50%, using a controlled humidity, degradation of log quality, because of cracking, checking and incipient rot, can be substantially prevented. The process in accordance with the invention provides a more uniform controlled, and less randomly variable moisture content than has heretofore been attainable. Consequently, subsequent processing, such as making veneer or plywood or cutting into lumber, produces higher yields, better quality recovery and fabrication is generally made easier.

It will, of course, be understood that modifications to the presently preferred embodiments will be apparent to those skilled in the art. Consequently, the scope of the present invention should not be limited by the particular embodiments discussed above, but should be defined only by the appended claims which are intended to cover all reasonable equivalents and are to be interpreted as broadly as the prior art will permit.

Having described the presently preferred embodiments, it is to be understood that the invention may be otherwise embodied by the scope of the claims appended hereto.

I claim:

1. A method for treating green wood comprising:

loading green wood into at least one hold of a ship equipped with means for introducing steam into the hold; and then contacting the wood with steam to raise the temperature of the wood to a sufficient level for a sufficient period of time to kill any plant pests present throughout the wood.

2. The method in accordance with claim 1 wherein the wood is selected from the group consisting of whole trees, logs, lumber, beams, timbers, cants, flitches, wood chips and wood strands.

3. The method in accordance with claim 2 wherein the wood is selected from the group consisting of logs, lumber, wood chips and wood strands.

4. The method in accordance with claim 3 wherein the wood is logs.

5. The method in accordance with claim 3 wherein the wood is wood chips or wood strands.

6. The method in accordance with claim 3 wherein the temperature of the center of the pieces of wood is raised to at least 56° C. and maintained at that temperature for at least 30 minutes.

7. The method in accordance with claim 6 wherein the wood has a volume of from about 15,000 cubic meters to about 35,000 cubic meters.

8. The method in accordance with claim 6 wherein the steam contains a chemical wood-treating ingredient selected from the group consisting of wood preservatives, fire retardants, fumigants, nematocides, fungicides and insecticides.

9. The method in accordance with claim 6 further comprising recycling water formed when the steam condenses back to the means for producing steam using a means for recycling spent steam operably connected between the hold and the means for introducing steam.

10. The method in accordance with claim 1 further comprising controlling the humidity in the hold during treatment, so that the final moisture content of the wood is kept at about 50% to maintain the fresh-cut characteristics of the green wood.

11. The method in accordance with claim 1 further comprising controllably reducing the moisture content of the wood to a predetermined level between about 30% and about 50%; and then maintaining the moisture content of the wood at the predetermined level to prevent the deterioration of the quality of the green wood.

12. A method for treating pieces of green wood comprising:

loading pieces of green wood into at least one hold of a ship, the ship equipped with means for producing hot water and means for creating a hot water shower in the hold with the hot water; and then contacting the pieces of wood with hot water having a temperature sufficient to raise the temperature of the wood to a sufficient level for a sufficient period of time to kill any plant pests present throughout the wood.

13. The method in accordance with claim 12 wherein the wood is selected from the group consisting of whole trees, logs, lumber, beams, timber, cants, flitches, wood chips and wood strands.

14. The method in accordance with claim 13 wherein the wood is selected from the group consisting of logs, lumber, wood chips and wood strands.

15. The method in accordance with claim 14 wherein the wood is logs.

16. The method in accordance with claim 13 wherein the wood is wood chips or wood strands.

17. The method in accordance with claim 14 wherein the temperature of the center of the pieces of wood is raised to at least 56° C. and maintained at that temperature for at least 30 minutes.

18. The method in accordance with claim 17 wherein the wood has a volume of from about 15,000 cubic meters to about 35,000 cubic meters.

19. The method in accordance with claim 17 wherein the hot water has a temperature of from about 60° C. to about 90° C.

20. The method in accordance with claim 19 wherein the hot water has a temperature of at least about 65° C.

21. The method in accordance with claim 17 wherein the hot water contains a chemical wood-treating ingredient selected from the group consisting of wood preservatives, fire retardants, fumigants, nematocides, fungicides and insecticides.

22. The method in accordance with claim 17 further comprising recycling water from the hold back to the means for producing hot water using a means for recycling spent hot water operably connected between the hold and the means for producing hot water.

23. The method in accordance with claim 10 further comprising controlling the humidity in the hold during treatment, so that the final moisture content of the wood is kept at about 50% to maintain the fresh-cut characteristics of the green wood.

24. The method in accordance with claim 10 further comprising controllably reducing the moisture content of the wood to a predetermined level between about 30% and about 50%; and then maintaining the moisture content of the wood at the predetermined level to prevent the deterioration of the quality of the green wood.

25. A method for preventing the deterioration of the quality of green wood comprising:

loading green wood into at least one hold of a ship equipped with means for introducing steam into the hold;

contacting the wood with steam while controllably reducing the moisture content of the wood to a predetermined level between about 30% and about 50%; and then maintaining the moisture content of the wood at the predetermined level to prevent the deterioration of the quality of the green wood.

26. The method in accordance with claim 25 wherein the wood is selected from the group consisting of whole trees, logs, lumber, beams, timbers, cants, flitches, wood chips and wood strands,

27. The method in accordance with claim 26 wherein the wood is selected from the group consisting of logs, lumber, wood chips and wood strands.

28. The method in accordance with claim 27 wherein the wood is logs.

29. The method in accordance with claim 27 wherein the wood is wood chips or wood strands.

30. A method for maintaining the fresh-cut characteristics of green wood comprising:

loading green wood into at least one hold of a ship equipped with means for introducing steam into the hold;

contacting the wood with steam; and maintaining the moisture content of the wood at about 50%% to maintain the fresh-cut characteristics of the green wood.

31. A method for preventing the deterioration of the quality of green wood comprising:

loading green wood into at least one hold of a ship equipped with means for introducing a shower of water having a temperature of from about 60° C. to about 90° C. into the hold;

contacting the wood with the water shower while controllably reducing the moisture content of the wood to a predetermined level between about 30% and about 50%; and then maintaining the moisture content of the wood at the predetermined level to prevent the deterioration of the quality of the green wood.

32. The method in accordance with claim 31 wherein the wood is selected from the group consisting of whole trees, logs, lumber, beams, timber, cants, flitches, wood chips and wood strands.

33. The method in accordance with claim 32 wherein the wood is selected from the group consisting of logs, lumber, wood chips and wood strands.

34. The method in accordance with claim 33 wherein the wood is logs.

35. The method in accordance with claim 33 wherein the wood is wood chips or wood strands.

36. A method for maintaining the fresh-cut characteristics of green wood comprising:

loading green wood into at least one hold of a ship equipped with means for introducing a shower of water having a temperature of from about 60° C. to about 90° C. into the hold;

contacting the wood with the hot water shower; and maintaining the moisture content of the wood at about 50% to maintain the fresh-cut characteristics of the green wood.

* * * * *